United States Patent [19]

Wright et al.

[11] Patent Number: 4,947,843
[45] Date of Patent: Aug. 14, 1990

[54] CARDIAC INSULATOR

[75] Inventors: John T. Wright, Conifer; Donald P. Elliott, Denver, both of Colo.

[73] Assignee: Pioneering Technologies, Inc., Wheat Ridge, Colo.

[21] Appl. No.: 313,602

[22] Filed: Feb. 21, 1989

[51] Int. Cl.$^5$ .............................................. A61F 7/12
[52] U.S. Cl. ...................................... 128/401; 128/846
[58] Field of Search ................. 128/64, 401, 403, 846, 128/400; 623/3; 600/16, 17

[56] References Cited

U.S. PATENT DOCUMENTS

| | | | |
|---|---|---|---|
| 3,717,199 | 2/1973 | Dienst | 128/401 |
| 4,154,245 | 5/1979 | Daily | 128/400 |
| 4,259,961 | 4/1981 | Hood | 128/400 |
| 4,536,893 | 8/1985 | Parravicini | 128/64 |
| 4,605,006 | 8/1986 | Jacques | 128/402 |
| 4,690,134 | 9/1987 | Snyders | 128/64 |
| 4,731,076 | 3/1988 | Noon et al. | 128/64 |

FOREIGN PATENT DOCUMENTS 1398858  5/1988  U.S.S.R. ............... 128/401

OTHER PUBLICATIONS

Dailey et al. "Clinical Comparisons of Methods of Myocardial Protection", J. Thorac Cariovasc. Jarg., vol. No. 93, 1987, pp. 324–336.
"Shiley Cardiac Insulation Pad", literature, copyright 1980, 3 sheets.

Primary Examiner—Edward M. Coven
Assistant Examiner—Graham
Attorney, Agent, or Firm—Grant L. Hubbard

[57] ABSTRACT

A single patient use disposable cardiac insulator to aid myocardial preservation during cardio-pulmonary bypass procedures which thermally insulates the myocardium from the pericardial cavity is disclosed.

12 Claims, 2 Drawing Sheets

CARDIAC INSULATOR

BACKGROUND OF THE INVENTION

This invention is directed at thermally insulating the heart during an open heart surgical procedure. The device reduces heat gain of the heart from its surroundings and further serves to protect the phrenic nerves from damage due to being exposed to low temperatures.

Surgical repair of occluded or semi-occluded coronary arteries by coronary artery bypass grafting, or repair or replacement of cardiac valves, as well as some other cardiac surgery is undertaken in conjunction with a cardio-pulmonary bypass procedure. During the period of cardio-pulmonary bypass the pumping function of the heart and the gas transfer function of the lungs are temporarily taken over by a heart-lung machine. During the period of cardiac surgery the myocardium is preserved by cooling of the heart to a temperature in the range of approximately 5°–15° Celsius. This cardiac cooling may be accomplished by substituting the normal coronary artery perfusion of warm blood by the infusion of a cold cardioplegia solution into the aortic root. In addition, the core temperature of the patient is usually lowered to 26°–28° C. to help reduce the temperature of the heart. The patient's body temperature is decreased (and subsequently raised) by means of a heat exchanger in the heart-lung machine. Topical cooling of the heart may also be used to reduce myocardial temperature. This may be accomplished by placing soft ice slush or cold saline solution on or around the heart, or by enclosing or partially enclosing the heart with a recirculating type cardiac cooler, such as are described in U.S. Pat. Nos. 4,154,245 and 4,259,961. Profound cardiac hypothermia is maintained for the duration of aortic cross clamping because various studies have shown that cardiac cooling has reduced the incidence of operative mortality. To maintain the temperature of the myocardium in the range of about 5°–15° C., it is necessary to reduce cardiac heat gain to a low level. Internal cardiac heat gain is minimized by preventing the perfusion of the heart with warm blood by cross-clamping the aorta distal to the coronary ostia. In some patients an extra coronary blood supply is thought to be by way of bronchial artery collaterals.

There are four possible sources of external cardiac heat gain. Firstly from the tissues surrounding the heart in the pericardial cavity. Usually this heat gain is reduced by lowering the patient's body temperature to approximately 26°–28° C., hence reducing heat flow into the heart. Secondly, from the air adjacent to the heart. Thirdly, from the surgeon's hands, and lastly from radiant heat from the operating room lights. Topical cooling has been used to reduce myocardial temperatures, and help negate the effects of heat gain from the four sources mentioned above. However, occasionally, the use of topical cooling by ice or a recirculating jacket has caused thermal damage to the phrenic nerves (which lie immediately adjacent to the lateral sides of the pericardial cavity). A cardiac insulator should thus both thermally insulate the heart and also offer thermal protection to the phrenic nerves. Effective thermal insulation of the myocardium from the chest cavity can also obviate the necessity for reducing the body temperature of the patient. Hence operative time spent during cooling and rewarming is eliminated, potentially reducing overall time of operation.

Cardiac insulators are known in the art. For example Shiley Laboratories, Inc., Santa Ana, California have such a pad in commercial distribution, and an experimental device (incorporating a cardiac insulator) was described by Daily, P. O.; Pfeffer, T. A.; Wisniewski, J. B.; Steinke, T. A.; Kinney, T. B.; Moores, W. Y.; and Dembitsky, W. P., Clinical comparisons of methods of myocardial protection, J. Thorac Cardiovasc Surg. Volume No. 93, 1987 pp. 324–336.

Although these devices, disclose the general principle of providing thermal insulation between the myocardium and the pericardial cavity, their particular construction creates difficulties in use. Namely, the former has several disadvantages. It is of such inappropriate shape that only part of the posterior and lateral portions and none of the anterior portion of the myocardium is insulated, and the phrenic nerves are not fully protected. Moreover the pad, being fully flexible, is difficult to insert under the adult heart, and has a marked tendency to slip around the pericardial cavity in use.

The cooling jacket described by Daily et al. (and another described in U.S. Pat. No. 4,154,245) incorporates a thin layer of insulating material, and a malleable skeleton, of different form and function to the semi-rigid stiffner used in this invention. In the Daily device the malleable metal skeleton allows the pad to be shaped around a portion of the diameter of the ventricular surfaces. Moreover the device described by Daily is not intended solely to act as a cardiac insulator, nor for use with soft ice slush or a cold saline solution applied as topical cardiac cooling, and as such offers no thermal protection of the phrenic nerves.

The semi-rigid stiffner used in the preferred embodiment of this invention is used to enable the device to be placed under the posterior myocardium, and retained in the appropriate anatomical location.

It is an objective of this invention to provide a myocardial thermal insulator.

It is a further objective of this invention to provide a thermal insulator to insulate the posterior, and lateral surfaces of the myocardium from the pericardial cavity.

It is a further objective of this invention to provide a thermal insulator to thermally protect the phrenic nerves from hypothermal injury due to topical cooling of the heart by soft ice slush, cold saline solution, or a recirculating type cardiac cooler. In the preferred embodiment of this invention it is a further objective of this invention to provide a myocardial thermal insulator containing a semi-rigid, malleable member which allows the surgeon easily to insert the device between the heart and the pericardial cavity.

It is a further objective of this invention to provide a thermal insulator to insulate the entire myocardium, and to thermally protect the phrenic nerves from hypothermal injury.

It is a further objective of this invention to provide a myocardial thermal insulator which may easily be inserted under the heart.

It is a further objective of this invention to provide a myocardial thermal insulator which will be retained in place under the heart.

It is still a further objective of this invention to provide a myocardial thermal insulator which will be retained in place around the heart.

It is still a further objective of this invention to provide a myocardial thermal insulator which will obviate the necessity of having to reduce the body temperature of the patient, hence potentially shortening overall time of the operation.

The simplicity and design of the cardiac insulator are such that it is quite inexpensive and hence may be disposable, hereby eliminating the necessity of cleaning and sterilizing between uses.

Other objects and advantages of this invention will be more apparent from the detailed description of the device which follows.

SUMMARY OF THE INVENTION

The invention comprises a single patient use disposable cardiac insulator to aid myocardial preservation during cardio-pulmonary bypass procedures which thermally insulates the myocardium from the pericardial cavity. The cardiac insulator of this invention may be used in conjunction with cardiac cooling by a cold cardioplegia solution, cold saline, soft ice slush, or a recirculating type cardiac cooler. The insulator is of a closed cell foam insulation to minimize cardiac heat gain from the posterior or lateral sides of the chest cavity. The insulator minimizes potential freezing of the phrenic nerve when ice slush, or a recirculating type cardiac cooler is used. It also potentially decreases the total time of operation by obviating the necessity for lowering the patient's body temperature.

In the preferred embodiment the insulator contains an internal malleable strip. This serves as a stiffener, allowing the insulator to be pushed easily under the heart. The stiffener is readily bent so that the insulator conforms to the posterior shape of the pericardial cavity.

Thus, the invention is directed to a cardiac insulating pad comprising of a specially shaped, closed cell, biocompatible, flexible foam.

In the preferred embodiment (which is of particular benefit for adult use) the device comprises of two membranes (one of which is a closed cell, biocompatible, flexible foam. Sandwiched between the two membranes is a semi-rigid member (preferably of a malleable nature) forming a backbone.

DETAILED DESCRIPTION OF THE DRAWINGS

For the purpose of illustrating the invention, there is shown in the drawings two forms which are presently preferred; it being understood, however, that this invention is not limited to the precise arrangements and instrumentalies shown.

DETAILED DESCRIPTION OF THE INVENTION

Figure 1:
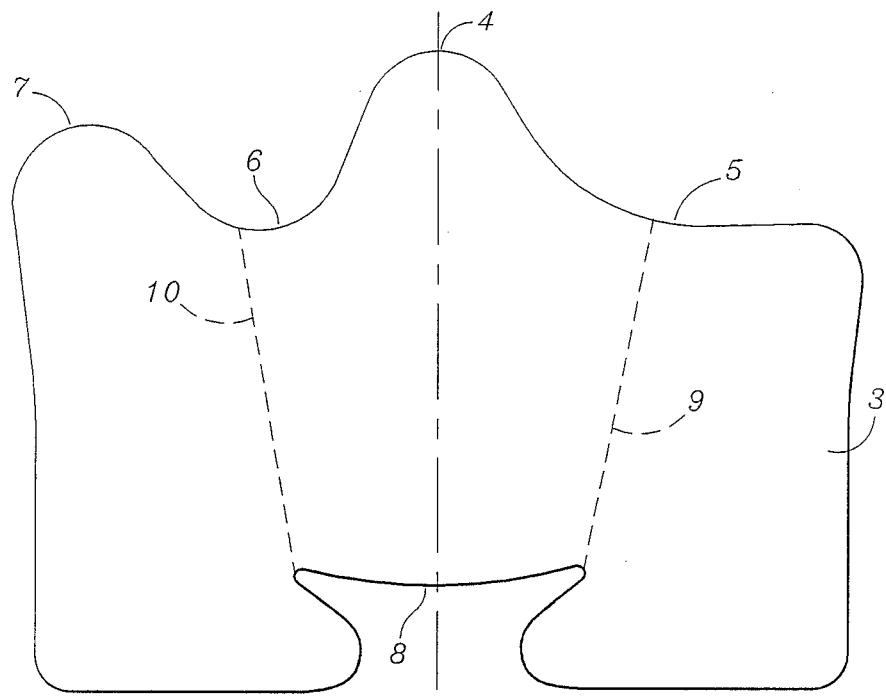
FIG. 1 is a plan view of the cardiac insulating device.
Figure 2:
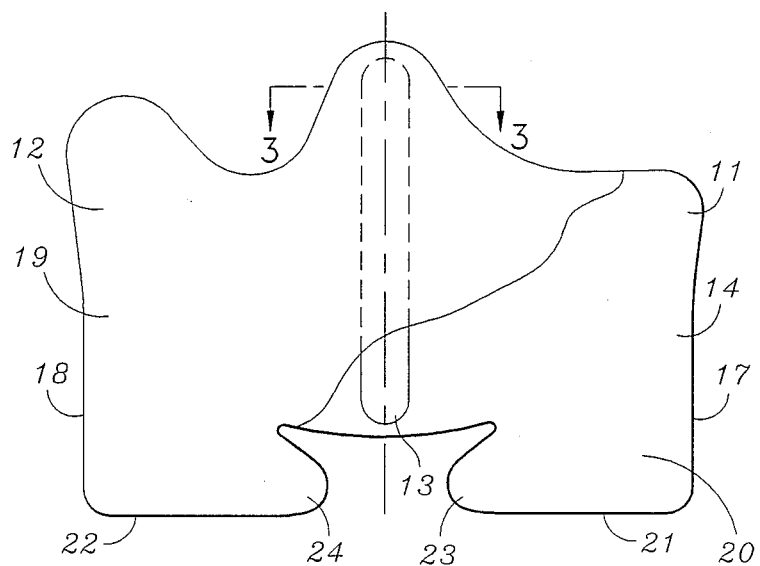
FIG. 2 is a plan view of the preferred embodiment of the cardiac insulating device containing a malleable stiffener having parts broken away for clarity.
Figure 3:
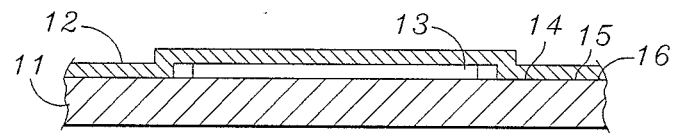
FIG. 3 is an enlarged part sectional view of the preferred embodiment of the device shown in FIG. 2, taken along line 3—3 of FIG. 2.
Figure 4:
FIG. 4 is an isometric view showing location of the cardiac insulating device relative to the heart.

Referring to the drawings wherein like numerals indicate like elements there is shown in FIG. 1 a cardiac insulator device designated as 3. The shape is of a generally rectangular configuration, but has certain recesses and excrescences which serve particular functions. Excrescence 4 is a protrusion to insulate the portion of the posterior myocardium which lies between the lower left pulmonary vein and the inferior vena cava. Recess 5 is to avoid interference with the lower left pulmonary vein, and recess 6 is to avoid interference with the inferior vena cava. Excrescence 7 is to insulate the lateral portion of the right atrium. Recess 8 is to allow the insulator to flex and fold approximately along lines 9 and 10 when inserted in the chest cavity. A plan view of the preferred embodiment of the invention is shown in FIG. 2, and an enlarged part sectional view of the preferred embodiment of the device shown in FIG. 3 (taken along line 2—2 of FIG. 2). Measuring approximately $10\frac{1}{4}''$ by 8" for a large adult size, the device consists of a flexible polyethylene foam membrane 11, joined to a second flexible membrane foam 12. Sandwiched between the two sheets is member 13, which serves as a stiffening spine, allowing the surgeon easily to push the device under the heart. The two flexible membranes may be joined by a biocompatible adhesive 14, or by other suitable means such as heat sealing or ultra sonic welding or radio frequency welding around their periphery and at suitable places adjacent to the member 13, thus retaining member 13 in a central position. In the preferred embodiment the first membrane 11 consists of a $\frac{1}{8}''$ thick layer of polyethylene foam material coated on side 15 with a layer of acrylic adhesive 16. To this adhesive layer is placed the soft, malleable, aluminum stiffner 13, and a second 1/32" thick layer of polyethylene foam material 12. The resulting sandwich is then die cut to shape, suitably packaged and sterilized. Sterilization may be by gamma or electron irradiation, or by exposure to ethylene oxide gas. Because member 13 is isolated from direct contact with tissues or cooling or body liquids, biological compatibility of the member is not necessary. In use, following commencement of cardio-pulmonary bypass the heart will usually be immobilized by perfusion of cold cardioplegia solution into the coronary arteries. When used in pediatric patients a reduced size cardiac insulator is appropriate. In these cases an internal malleable stiffener in not required because the surgeons fingers are of appropriate length to allow the device easily to be pushed under the child heart. However, in adult patients, the heart is of such a size (especially in the case of certain or advanced valvular diseases) that the internal malleable stiffner is a significant advantage in the placement and retention of the device. The use of the device in an average adult patient will be described. However, it being assumed that the placement of the device in the chest cavity of a child will be similar, but that in the smallest sizes the use of the internal malleable stiffener is not necessary. The device will be held by the surgeon with the thin membrane 12 uppermost. The left side of the device 19 will be folded approximately along line 10 to lay over the internal stiffner 13. Similarly the right side 20 will be folded approximately along line 9 to lay above the folded left side 19, also above the internal stiffner 13. The surgeon will then bend the folded device in a gently concave arc. The apex of the heart is lifted and the portions 4 and 7 of the insulator carefully pushed fully under the heart, unfolding the device as it is inserted. Slight axial force on the distal end of the internal stiffner will aid in pushing the device fully under the heart. The insulator should be positioned so as not to interfere with the left pulmonary veins or venous return from the inferior vena cava. The malleable stiffener 13 should then be bent so that the insulator conforms to the posterior pericardial cavity. The insulator will flex approximately along lines 9 and 10 such that portions 17 and 18 lie roughly vertically to form sides that come together at 21 and 22.

Ice slush, cold saline, or a recirculating cardiac cooling jacket may then be placed into the space between the heart and the insulator. The white reflective surface of the insulator improves lighting in the chest cavity, and enhances the visibility of the fine sutures used to anastomose the coronary grafts in situ. In valve replacement surgery, when access to the coronary arteries is not required, the portions of the insulator designated 23 and 24 may be folded across the anterior myocardium and retained by sutures or instruments (such as forceps) to shield the anterior myocardium from radiant heat gain from the operating room spotlights.

The insulator is removed from the patient's chest cavity at the conclusion of surgery before whole body warming is commenced. The cardiac insulator could be manufactured to a range of sizes appropriate for various adult hearts, or to suit the surgeon's preference.

The present invention comprises a cardiac insulator consisting essentially of a membrane construction of from about 1/32 inch to about ½ inch a thickness, the membrane construction defining a generally rectangular configuration of up to about 8 inches in width and about 10¼ inches in length and first and second long sides and first and second short sides. The periphery of the membrane construction is constructed and configured so as to define five distinct peripheral configurational structures.

A first excrescence (4) is defined approximately central of the first long side of the membrane construction. The first excrescence is so constructed and configured as to insulate the portion of the posterior myocardium which lies between the lower left pulmonary vein and the inferior vena cava when the cardiac insulator is in use positioned about a human heart.

A first recess (5) is also defined on the first long side on one side of the first excrescence. The first recess being so configured as to avoid interference with the lower left pulmonary vein when the cardiac insulator is in use positioned about a human heart.

A second recess (6) is also defined on the first long side and on the other side of the first excrescence. The second recess being so configured as to avoid interference with the vena cava when the cardiac insulator is in use positioned about a human heart.

A second excrescence 7 is also defined on the first long side spaced from the first excrescence by the second recess. The second excrescence being so constructed and configured as to insulate the lateral portion of the right atrium when the cardiac insulator is in use positioned about the human heart.

A third recess (8) is defined approximately central of the second long side of the membrane construction. The third recess being so formed and configured to allow the insulator to flex and fold when the cardiac insulator is in use positioned about the human heart and to define two portions (23 and 24) which extent toward each other from the first and second short sides, respectively, of the membrane construction. The portions 23 and 24 are so constructed and configured as to be folded across the anterior myocardium to shield the anterior myocardium from radiant heat gain from operating room spotlights when the cardiac insulator is in use positioned about the human heart.

The cardiac insulator comprises at least one layer of flexible polymeric foam membrane so configured as to thermally insulate substantially all of the posterior and lateral surfaces of the myocardium from the pericardial cavity, and to insulate both left and right phrenic nerves from the effects of cold substances or devices placed between the myocardium and said insulator.

The cardiac insulator, in one preferred embodiment, is comprised of two flexible polymeric foam membranes and further comprises a malleable stiffening member sandwiched between the two flexible polymeric foam membranes.

INDUSTRIAL APPLICATION

This invention is useful in surgical procedures.

We claim:

1. A cardiac insulator having a generally rectangular configuration, having dimension up to about 10 inches by 8 inches, defining:
   (a) a first excrescence means (4) constructed and configured so as to insulate the portion of the posterior myocardium which lies between the lower left pulmonary vein and the inferior vena cava when the cardiac insulator is in use positioned about a human heart;
   (b) a first recess means (5) so formed and configured to avoid interference with the lower left pulmonary vein when the cardiac insulator is in use positioned about a human heart;
   (c) a second recess means (6) so formed and configured to avoid interference with the vena cava when the cardiac insulator is in use positioned about a human heart;
   (d) a second excrescence means 7 constructed so as to insulate the lateral portion of the right atrium when the cardiac insulator is in use positioned about the human heart; and
   (e) a third recess means (8) so formed and configured to allow the insulator to flex and fold when the cardiac insulator is in use positioned about the human heart;
   the cardiac insulator comprising at least one layer means of flexible polymeric foam membrane so configured as to thermally insulate substantially all of the posterior and lateral surfaces of the myocardium from the pericardial cavity, and to insulate both left and right phrenic nerves from the effects of cold substances or devices placed between the myocardium and said insulator.

2. The cardiac insulator of claim 1 wherein the cardiac insulator is comprised of two flexible polymeric foam membranes and further comprises: a malleable stiffening member sandwiched between the two flexible polymeric foam membranes.

3. The cardiac insulator of claim 2 wherein at least one of said membranes comprises a flexible closed cell polymeric foam membrane having a thickness of from about 1/32 to 15/32 inch.

4. The cardiac insulator of claim 1 wherein the cardiac insulator is comprised of two flexible polymeric foam membranes and further comprises: a malleable stiffening member sandwiched between the two flexible polymeric foam membranes and adhesively bonded to at least one of such membranes.

5. The cardiac insulator of claim 1 wherein the cardiac insulator is comprised of two flexible closed cell polymeric foam membranes each having a thickness of from about 1/32 to 15/32 inch, the total thickness of both membranes being not greater than ½ inch.

6. The cardiac insulator of claim 1 wherein the cardiac insulator is comprised of two flexible closed cell polymeric foam membranes each having a thickness of from about 1/32 to 15/32 inch, the total thickness of both membranes being not greater than ½ inch, and further comprises: a malleable stiffening member sandwiched between the two flexible polymeric foam membranes and adhesively bonded to at least one of such membranes.

7. A cardiac insulator consisting essentially of:
(a) a membrane construction of from about 1/32 inch to about ½ inch in thickness, the membrane construction defining a generally rectangular configuration of up to about 8 inches in width and about 10¼ inches in length and first and second long sides and first and second short sides, the periphery of the membrane construction being so constructed and configured so as to define:
 (i) a first excrescence means (4) approximately central of the first long side of the membrane construction, said first excrescence means being so constructed and configured as to insulate the portion of the posterior myocardium which lies between the lower left pulmonary vein and the inferior vena cava when the cardiac insulator is in use positioned about a human heart;
 (ii) a first recess means (5) on the first long side on one side of the first excrescence means, the first recess means being so configured as to avoid interference with the lower left pulmonary vein when the cardiac insulator is in use positioned about a human heart;
 (iii) a second recess means (6) on the first long side and on the other side of the first excrescence means, the second recess means being so configured as to avoid interference with the vena cava when the cardiac insulator is in use positioned about a human heart;
 (iv) a second excrescence means 7 on the first long side spaced from the first excrescence means by the second recess means, the second excrescence means being so constructed and configured as to insulate the lateral portion of the right atrium when the cardiac insulator is in use positioned about the human heart;
 (v) a third recess means (8) approximately central of the second long side of the membrane construction, the third recess means being so formed and configured to allow the insulator to flex and fold when the cardiac insulator is in use positioned about the human heart and for defining two portion means (23 and 24) which extend toward each other from the first and second short sides, respectively, of the membrane construction, said portion means being so constructed and configured as to be folded across the anterior myocardium to shield the anterior myocardium from radiant heat gain from operating room spotlights when the cardiac insulator is in use positioned about the human heart;
the cardiac insulator comprising at least one layer means of flexible polymeric foam membrane so configured as to thermally insulate substantially all of the posterior and lateral surfaces of the myocardium from the pericardial cavity, and to insulate both left and right phrenic nerves from the effects of cold substances or devices placed between the myocardium and said insulator.

8. The cardiac insulator of claim 7 wherein the cardiac insulator is comprised of two flexible polymeric foam membranes and further comprises: a malleable stiffening member sandwiched between the two flexible polymeric foam membranes.

9. The cardiac insulator of claim 8 wherein at least one of said membranes comprises a flexible closed cell polymeric foam membrane having a thickness of from about 1/32 to 15/32 inch.

10. The cardiac insulator of claim 7 wherein the cardiac insulator is comprised of two flexible polymeric foam membranes and further comprises: a malleable stiffening member sandwiched between the two flexible polymeric foam membranes and adhesively bonded to at least one of such membranes.

11. The cardiac insulator of claim 7 wherein the cardiac insulator is comprised of two flexible closed cell polymeric foam membranes each having a thickness of from about 1/32 to 15/32 inch, the total thickness of both membranes being not greater than ½ inch.

12. The cardiac insulator of claim 7 wherein the cardiac insulator is comprised of two flexible closed cell polymeric foam membranes each having a thickness of from about 1/32 to 15/32 inch, the total thickness of both membranes being not greater than ½ inch, and further comprises: a malleable stiffening member sandwiched between the two flexible polymeric foam membranes and adhesively bonded to at least one of such membranes.

* * * * *